United States Patent [19]

Chew, III

[11] 4,149,804
[45] Apr. 17, 1979

[54] METHOD AND APPARATUS FOR MEASURING CHEMICAL CONTENT OF CORE SAMPLES

[75] Inventor: Randall T. Chew, III, Grand Junction, Colo.

[73] Assignee: Occidental Oil Shale, Inc., Grand Junction, Colo.

[21] Appl. No.: 764,858

[22] Filed: Feb. 2, 1977

[51] Int. Cl.² .................. G01J 3/50; G01N 21/48
[52] U.S. Cl. .............. 356/416; 23/230 EP; 356/36; 356/448;
[58] Field of Search ........... 23/230 EP; 250/301, 250/339–341,372; 356/70; 186; 201; 204–206; 209–212; 36; 38; 51

[56] References Cited

U.S. PATENT DOCUMENTS

| 3,232,711 | 2/1966 | Senyk et al. | 356/38 X |
| 4,009,962 | 3/1977 | Lauer et al. | 356/70 X |
| 4,030,837 | 6/1977 | Kojima et al. | 356/209 |

Primary Examiner—F. L. Evans
Attorney, Agent, or Firm—Christie, Parker & Hale

[57] ABSTRACT

A field instrument for measuring the chemical composition of a solid core sample includes means for forming a smooth surface along the core sample, a light source for illuminating the smoothed surface, a photocell for sensing monochromatic light reflected from the surface of the core sample, means for providing relative movement between the core sample and the photocell, and means for converting the photocell output into a measurement of the amount of a chemical component being analyzed contained in the core sample. To avoid wide variations in measured chemical content, caused by non-uniform distribution of the material being analyzed within the core sample, reflected light is integrated over a selected area of the core sample.

45 Claims, 9 Drawing Figures

METHOD AND APPARATUS FOR MEASURING CHEMICAL CONTENT OF CORE SAMPLES

BACKGROUND

This invention relates to a method and apparatus for measuring the chemical content of solid core samples. More particularly, the core sample analysis of this invention can be performed immediately without requiring laboratory analysis and calculations, or destructive techniques.

The present invention is described herein in the context of a method and apparatus for measuring the kerogen content of oil shale, although the method and apparatus can be used to measure the content of other elements, compounds, or groups of compounds in other solid core samples.

Vast untapped reserves of oil entrapped in oil shale exist in this country as well as other locations throughout the world. Increased attention is being devoted to the exploitation of oil shale because of the current need for new energy sources.

The term "oil shale" as used in the industry is in fact a misnomer, because it is neither shale, nor does it contain oil. It is a sedimentary formation comprising marlstone deposits interspersed with layers containing an organic polymer called "kerogen" which upon heating decomposes to produce carbonaceous liquid and gaseous products. It is the formation containing kerogen that is called "oil shale" herein, and the carbonaceous liquid product is called "shale oil."

Oil shale deposits occur in generally horizontal beds, and within a given bed there are an extremely large number of generally horizontal deposition layers containing kerogen known as "varves." The varves typically are non-uniformly dispersed throughout a given bed. In the higher grade oil shales, the varves are commonly cemented together into relatively thick, compact layers. The lower grade oil shales have much thinner varves spaced apart through the bed. For example, a core sample taken from a typical bed may vary from thick, solid oil shale sections to layered sections having the appearance of poker chips. In the core, small layers or nodules of other minerals and rock materials are sometimes found interspersed between the varves containing kerogen. Typical of these other minerals are nahcolite, dawsonite, other salines, dolomite, mudstone, sandstone, tuffs, analcite and bentonite.

Techniques for preparing shale oil for retorting generally comprise explosively expanding a subterranean oil shale formation to form a fragmented, permeable mass of oil shale particles. Shale oil then may be recovered from the particles by in situ retorting techniques, or by retorting in surface retorts, for example.

Prior to preparing the oil shale for retorting, the formation is explored to determine the locations within the formation containing the highest grades of oil shale. Core samples are taken from the formation and subjected to laboratory analysis to determine the kerogen content of the sample. One such analytical technique is the "Fischer assay" in which a sample customarily weighing 100 grams and representing one foot of core is subjected to controlled laboratory analysis involving grinding the sample into small particles which are placed in a sealed vessel and subjected to heat at a known rate of temperature rise to measure the kerogen content of the core sample. Kerogen content is usually stated in units of "gallons per ton," referring to the number of gallons of shale oil recoverable from a ton of oil shale heated in the same manner as the Fischer analysis.

Such analytical techniques are generally done in laboratories far from the drilling site. This causes a considerable delay before analytical results are available to field personnel conducting the exploration tests. Thus, immediate field decisions on the progress of the exploration program cannot be based on accurate analyses of core samples.

The present invention provides a method and apparatus for rapidly determining the chemical composition of a core sample. For example, the kerogen content of oil shale can be rapidly measured without requiring calculations or destructive laboratory techniques characteristic of the Fischer assay and other known methods for measuring kerogen content. The invention makes it possible to accurately analyze a core sample in the field and still have the core sample available for other purposes, such as corroborating laboratory measurements to be conducted later at a more convenient time. Thus, field decisions on the progress of the exploration program can be made immediately, rather than waiting for several days, which is a common delay for current kerogen analysis techniques, for example.

SUMMARY OF THE INVENTION

According to a presently preferred embodiment of the invention, the chemical content of a solid core sample is measured by a method and apparatus for illuminating a surface of the core sample to reflect the light not absorbed by the sample. The amount of light absorbed by the sample is proportional to the amount of a material to be analyzed contained in the sample and is measured by detecting the amount of light reflected from the illuminated surface. The light which is detected is essentially monochromatic light within the absorption band for the material under analysis. The amount of monochromatic light detected is indicated as a value proportional to the content of the material being analyzed contained in the core sample. A given core sample will reflect a specific amount of light when the sample is illuminated with light at a given wavelength. The detected light is converted into a measurement of chemical content based on a corresponding measurement of light reflected at the same wavelength from a reference core sample having a known chemical content.

In analyzing an elongated core sample, a selected surface area of the core sample is illuminated. The amount of light reflected from the illuminated area is detected and converted into a measurement of chemical content in the illuminated area of the sample. The chemical content distribution with respect to the length of the core sample can be determined. To avoid wide variations in the measurement of chemical content along a given sample, caused by non-uniform distribution of the material being analyzed within the core sample, the light reflected from the core sample is integrated. In one form of the invention, reflected light is integrated by spatial integration techniques. In another form of the invention, reflected light is integrated with respect to time.

According to one form of the invention, immediate analyses of the chemical content of solid core samples are provided by initially forming a smooth reflective surface of a predetermined generally uniform configuration along the length of a core sample. The smoothed surface is thereafter illuminated, and the amount of light reflected from the illuminated surface is detected, preferably by relative movement between the sample and the light detecting means. The detected light is essentially monochromatic light within the absorption band of the material under analysis. The detected light can be converted into a measurement of the distribution of the material being analyzed relative to the length of the core sample, knowing the specific amount of light, at the wavelength of the detected light, which is reflected from a sample of known chemical content.

These and other aspects of the invention will be more fully understood by referring to the following detailed description and the accompanying drawings.

DETAILED DESCRIPTION

This invention is based on a recognition that the kerogen content of oil shale is proportional to the amount of light, of a selected wavelength, absorbed by the oil shale. A solid core sample of oil shale can be immediately and non-destructively analyzed for kerogen content, according to a presently preferred embodiment of this invention, by illuminating a surface of the sample with light having a monochromatic component within the absorption band for kerogen in oil shale, and detecting the amount of light absorbed by the sample. Preferably, the amount of light absorbed is detected by sensing the amount of light reflected by the illuminated surface of the core sample. The reflected light is inversely proportional to the amount of light absorbed and also inversely proportional to the kerogen content in the portion of the sample being illuminated. The amount of said monochromatic light in the light reflected from the surface is detected and converted into a measurement proportional to the kerogen content of the sample. The amount of kerogen in the sample is determined by comparing the amount of light reflected from the sample with the amount of light, at the same wavelength reflected from a reference piece of oil shale having a known kerogen content.

The term "light" is used herein to mean light energy not only in the visible spectrum, but also light extending into the ultraviolet and infrared spectra. The term "monochromatic light" is meant to include light of a discrete wavelength, or at least light in a narrow wavelength band, say of 25 nanometers or less. The term "solid sample of oil shale" is defined herein to mean an intact piece of oil shale as distinguished from powdered. The solid piece can have some cracks or delaminations as long as they do not absorb light to the extent of producing appreciably misleading results.

The kerogen content of a sample of oil shale is measured by detecting the amount of monochromatic light absorbed by the sample, in which the monochromatic light has a wavelength within the absorption band for the kerogen contained in the particular type of oil shale under analysis. The presently preferred wavelength for analyzing oil shale from the Piceance Creek Basin in Colorado and Utah is within the range of about 260 to about 500 nanometers, i.e., at the low end of the visible spectrum and part of the near ultraviolet spectrum. The preferred discrete wavelength is about 420 nanometers. This wavelength is preferred because of its relatively good sensitivity in discerning variations in kerogen content over a relatively wide range of potential kerogen concentrations in a piece of oil shale.

Figure 5:
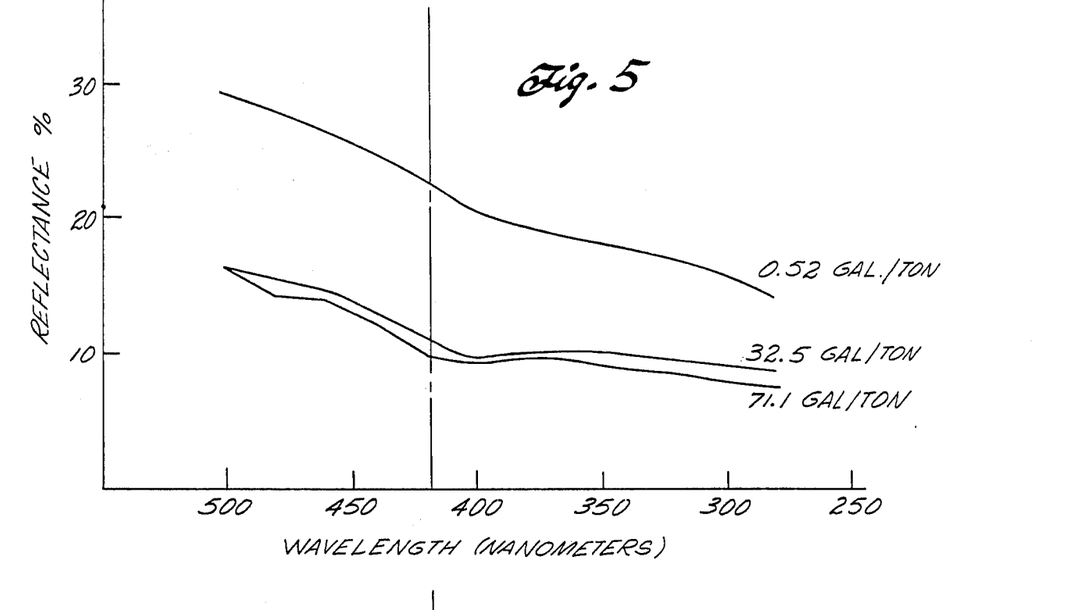
FIG. 5 is a graph illustrating the relationship between light wavelength and light reflectance from oil shale core samples of varying known kerogen content, using magnesium oxide as a standard for 100% reflectance.

The presently preferred wavelength of the light used to measure kerogen content was determined according to the following procedure. Smooth surfaces of identical configuration and size were formed on several core samples of oil shale having known kerogen contents. The surface of each sample was then illuminated with monochromatic light, and the amount of light reflected from the surface of each sample was sensed by a photocell. The wavelength of the monochromatic light source was varied in increments of 20 nanometers, and reflectance for each increment was sensed. In one test, samples ranging in known kerogen content from 0.52 gallons per ton to 71.1 gallons per ton were analyzed. The known kerogen content of the samples was initially determined over one foot of core using Fischer assay techniques. The samples were then examined using wavelengths ranging from about 280 to about 500 nanometers. Magnesium oxide was used as a standard for 100% reflectance. A Beckman DU Spectrophotometer was used to measure reflectance from a 0.75-inch diameter circle on each sample. The test results are illustrated in the graph shown in FIG. 5. The results showed a consistent decrease in the amount of light reflected (reflectance) from the surface of the oil shale as the grade or kerogen content of oil shale increased. The difference in measured reflectance between the highest and lowest assays was generally greatest at a wavelength of about 420 nanometers (indicated in phantom line in FIG. 5), although the test results also showed good sensitivity at a wavelength of about 480 nanometers.

Figure 6:
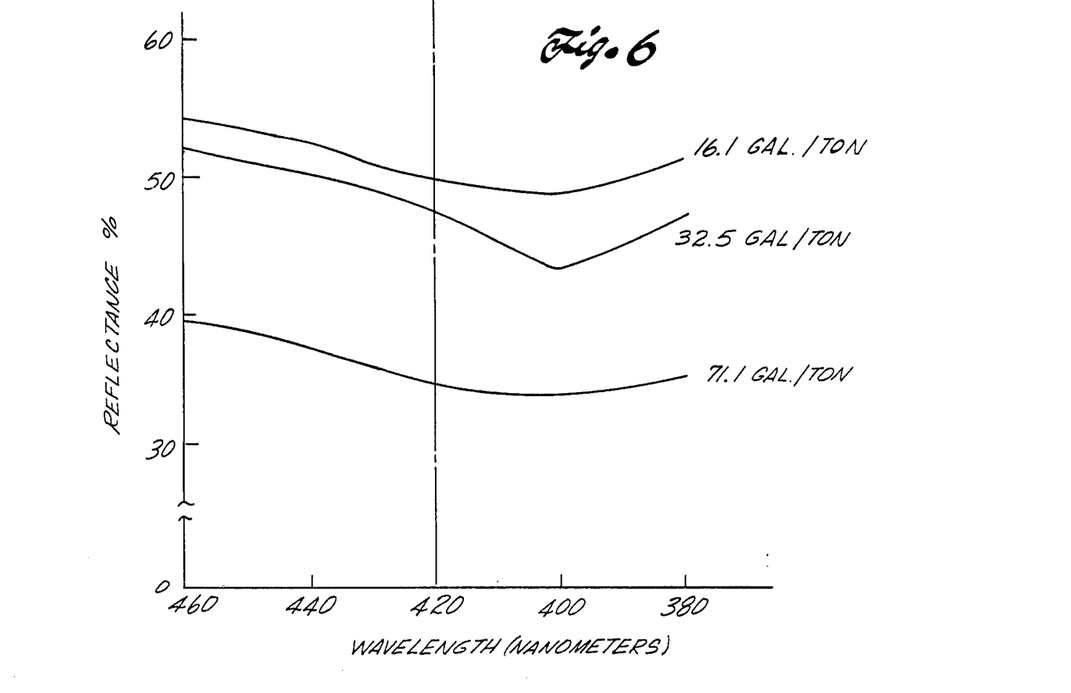
FIG. 6 is a graph illustrating the relationship between light wavelength and the light reflectance from oil shale core samples of varying known kerogen content, using barren marlstone as a standard for 100% light reflectance.

In a separate test, the reflectance of several samples ranging in known kerogen content from 16.1 gallons per ton to 71.1 gallons per ton was conducted using a marlstone sample of zero kerogen content as a standard for 100% reflectance. The samples were examined using wavelengths varied in increments of 20 nanometers in a range of about 380 to 460 nanometers. The test results are illustrated in FIG. 6 and again showed a trend toward decreasing reflectance with increasing kerogen content. The greatest sensitivity in reflectance measurements among the samples tested generally occurred at a wavelength of about 420 nanometers (indicated in phantom line in FIG. 6).

Thus, a given core sample will reflect a specific amount of light when the sample is illuminated with light at a given wavelength, and the presently preferred wavelength for light used to measure kerogen content in the type of oil shale under analysis is about 420 nanometers. This wavelength generally exhibits a good range of light absorption (or reflectance) as a function of kerogen assay, i.e., the greatest sensitivity to changes in kerogen concentration for the samples tested.

Figure 1:
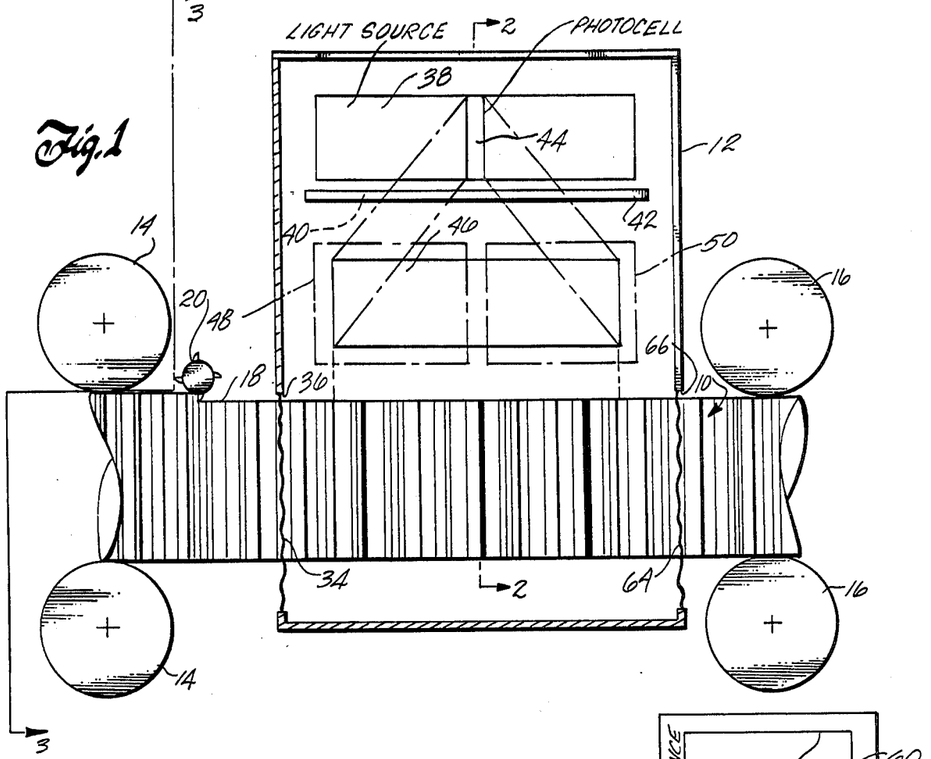
FIG. 1 is a fragmentary, schematic elevation view illustrating a presently preferred method and apparatus for measuring the kerogen content of an oil shale core sample according to principles of this invention.
Figure 2:
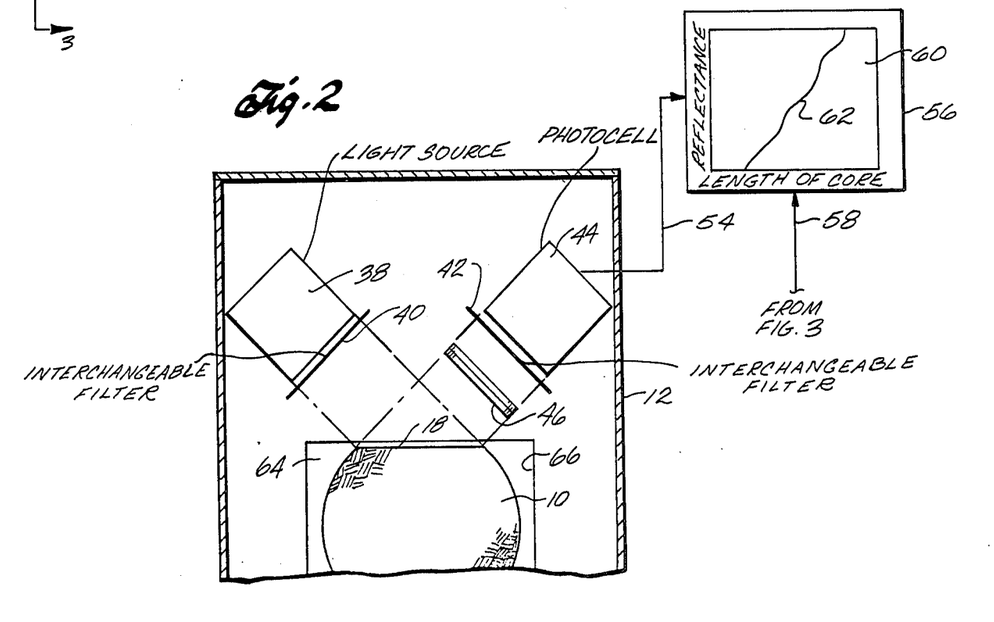
FIG. 2 is a schematic cross-sectional view taken on line 2—2 of FIG. 1.
Figure 3:
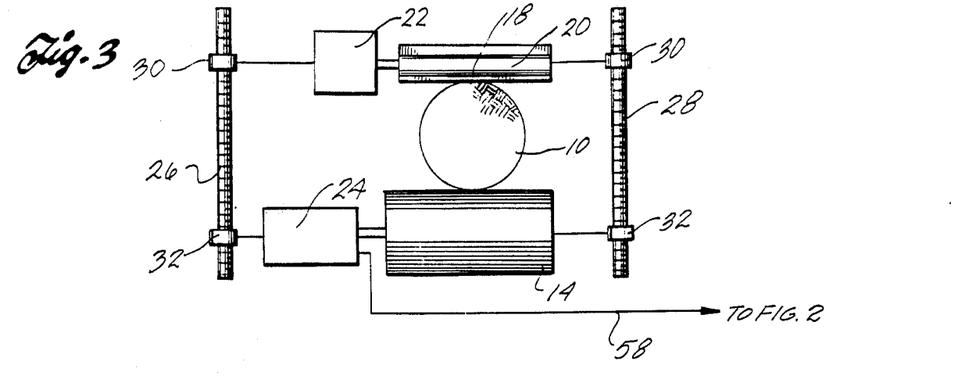
FIG. 3 is a schematic cross-sectional view taken on line 3—3 of FIG. 1.

FIGS. 1 through 3 illustrate a presently preferred field instrument for rapidly measuring the kerogen content of oil shale. The field instrument also can be used to measure the amount of any material contained in a solid core sample, as long as the material being analyzed absorbs or reflects light in proportion to its concentration in the core sample when a surface of the sample is illuminated with light having a monochromatic component within the absorption band of the material being analyzed.

The following description of the field instrument will be in the context of its use in measuring the kerogen content of an elongated cylindrical core sample 10 of solid oil shale obtained by standard rock core drilling procedures from the Piceance Creek Basin. The core sample 10 is moved lengthwise through a stationary, essentially light-tight housing 12 in which the core sample is illuminated by a light source having the desired monochromatic component necessary to analyze kerogen content. The core sample is moved through the housing 12 by drive rollers 14 which apply pressure to the top and bottom surfaces of the core sample to force the sample through an entrance to the housing 12. Idler rollers 16 spaced longitudinally from the drive rollers 14 apply pressure to the top and bottom of the core sample 10 and support the core sample as it passes away from the housing 12.

Prior to moving the core sample 10 through the housing 12, a smooth reflective surface 18 of selected configuration is formed along the top surface of the core sample. The smooth reflective surface 18 reduces light scattering from subsequent illumination of the surface. Preferably, the reflective surface 18 is continuously formed by a rotary milling cutter 20 which mills a narrow, flat surface on the core sample 10 immediately before the core sample is fed through the housing 12. A tungsten carbide tipped milling cutter is preferred to minimize effects of wear by the oil shale. It will be understood that the milling cutter is illustrated schematically with drawings. The milling cutter 20 forms a flat surface of uniform width, preferably about ⅜ to about ½ inch wide, along the length of core sample 10. As shown best in FIG. 3, a drive motor 22 rotates the milling cutter 20, and a separate drive motor 24 rotates the drive rollers 14.

Alternatively, a diamond trim saw may be used to form a flat, smooth reflective surface lengthwise along the core sample. Further, the reflective surface can be formed by cutting a core sample in half lengthwise along its diameter.

The flat, smooth surface 18 need not be formed if all core samples to be analyzed are of the same surface configuration and are relatively smooth so that appreciable light scattering is avoided.

The relative spacing between the lower drive roller 14 and the milling cutter 20 is adjustable to accommodate core samples of different diameter. The spacing between the upper and lower drive rollers 14 also can be adjusted. FIG. 3 schematically illustrates a presently preferred position-adjusting mechanism, although a variety of structures may be used to adjust the spacing between a milling cutter and its drive means. The position-adjusting mechanism illustrated in the drawings includes upright threaded shafts 26 and 28 adjacent opposite edges of the core sample 10. A pair of upper position-adjusting devices (represented schematically at 30) are engaged with the upper portions of the threaded shafts 26, 28 on opposite sides of the core sample. The upper position-adjusting devices 30 can be a pair of sleeves loosely fitted around the threaded shafts 26, 28 and engaged with adjusting nuts for being turned relative to the threaded shafts to adjust the position of the milling cutter 20 and its drive motor 22 relative to both the core sample 10 and the lower drive roller 14. A pair of similar lower position-adjusting devices (represented schematically at 32) are engaged with the lower portions of the threaded shafts 26, 28. The lower position-adjusting devices 32 are engaged with adjusting nuts for being turned relative to the threaded shafts 26, 28 to adjust the position of the lower drive roller 14 relative to the core sample 10, the milling cutter 20, and the upper drive roller 14. A similar adjusting mechanism (not shown) adjusts the elevation of the lower idler roller 16 and the spacing between the upper and lower idler rollers 16.

After passing under the milling cutter 20, the core sample 10 passes through a first light-tight curtain 34 covering an entrance opening 36 in the housing 12. An electric light source 38 located in the upper interior portion of the housing 12 illuminates a selected area on the flat reflective surface 18 as the core sample travels through the housing 12. The light source 38 generates light (as defined above) which includes a wavelength within the light absorption band for kerogen in oil shale. In the presently preferred form of the invention, the light source 38 is an ultraviolet fluorescent lamp. The light from the lamp passes through a first filter 40 disposed between the light source and the reflective surface 18 of the core sample 10. The filter 40 is a narrow bandpass filter which passes monochromatic light, preferably light having a wavelength of about 420 nanometers. Alternatively, a monochromatic light source, without light filtering means, can be used, as long as the wavelength of the light produces a useful degree of sensitivity, in terms of measured reflectance, to a relatively wide range of kerogen concentrations likely to be encountered in oil shale.

As illustrated in FIG. 2, the light source 38 is mounted at an angle with respect to a vertical plane through the longitudinal axis of the reflective surface 18 formed on the core sample 10. Light which is not absorbed by the core sample 10 is reflected from the reflective surface 18 and passes through a second filter 42 prior to being sensed by a photocell 44. The second filter 42 passes the same wavelength as that passes by the first filter 40.

Alternatively, only one light filter can be used. In this instance, the filter is on the photocell side of the instrument to ensure preventing any stray light from being sensed by the photocell.

The filters 40 and 42 are removably mounted in the housing 12 so that they can be replaced with other filters for passing monochromatic light of other selected wavelengths. For example, oil shale from different locations can have different light absorption bands dependent upon the type of kerogen contained in them, and core samples of materials other than oil shale also will have different light absorption bands depending upon the chemical component being analyzed; and the field instrument herein enables the user to test analyze the core sample for light absorption at selected wavelengths and select the filter passing the wavelength which yields results having the greatest sensitivity in terms of reflectance measurements for the particular core sample under analysis.

The photocell 44 is located within the upper interior portion of the housing 12. The photocell 44 detects only the light reflected from the illuminated area of the core sample. The photocell 44 produces an electrical output having a magnitude directly proportional to the amount of sensed reflected light, and therefore inversely proportional to the amount of light absorbed by the core sample. The relationship between reflectance (absorption) and kerogen concentration is essentially linear over a relatively wide range of kerogen concentrations likely to be encountered in oil shale. Hence, the measurement of light reflectance provides a reliable indication of kerogen content for a given core sample.

FIGS. 1 through 3 illustrate a presently preferred system for integrating the amount of light reflectance (absorption) over a selected area of the core sample. The light integration system is used because of the typically non-homogeneous concentration of kerogen in any given sample of oil shale. That it, kerogen is often dispersed in randomly spaced apart varves of different concentrations and random width along the length of a core sample of oil shale. If a relatively narrow area of the core sample is illuminated at any given time, then resulting reflectance measurements can exhibit relatively wide variations in kerogen content along the length of the core sample. The light integration system senses illumination from a relatively wide area likely to contain numerous varves of kerogen to avoid large amplitude variations in measured kerogen content due to the typically non-uniform distribution of kerogen. This system gives a spatial integration of kerogen content in a sample of oil shale.

In the integration system of FIGS. 1 through 3, the light source 38 is elongated and is mounted so as to illuminate the entire width, and a one-foot length, of the core sample reflective surface 18. The length of one foot is chosen to correspond to the one-foot length of core often used to determine kerogen content by Fischer assay techniques. In integrating the light over one-foot lengths, the core sample can be illuminated intermittently over the one-foot lengths, with the amount of reflected light for each one-foot length being intermittently sensed and recorded. However, other lengths of the core sample 10 can be illuminated by the light source 38, or the light source 38 can be used in combination with a lens system (not shown) to direct incident light onto a selected area of the core sample. Further, the light integration can be continuous as well as intermittent.

The presently preferred light integration system also includes a lens 46 (illustrated schematically) between the core sample and the second filter 42. The lens 46 focuses on the photocell 44 the light reflected from the illuminated area of the core sample. Preferably, the lens 46 is a cylindrical lens for focusing on the photocell 44 all of the light reflected from the essentially rectangular, one-half inch wide, one-foot long area illuminated by the light source 38. The entire amount of focused light sensed by the photocell 44 at any time is proportional to the average amount of reflectance along the one-foot length of core at that time. A one-foot length of core is likely to contain numerous varves containing kerogen. Spatial integration of the reflectance over this length of core sample produces a measurement of the average kerogen content of the one-foot sample, independently of whether the core sample contains a highly non-uniform kerogen distribution.

If it is desired to analyze only a narrow length of core, or if the core sample to be analyzed is less than one foot long, a pair of spaced apart movable blinders 48 and 50 (illustrated in phantom lines in FIG. 1) can be used to block the passage of light from the core sample to part of the surface of the lens 46. The blinders 48 and 50 can be spaced apart by any selected distance to adjust the area of illumination sensed by the photocell.

Light integration systems other than the light focusing lens system of FIGS. 1 through 3 can be used. For example, a suitably arranged system of mirrors (not shown) can be located in the housing to collect light reflected from a relatively larger area of the core sample and focus the light on the relatively smaller area of the photocell 44.

The photocell 44 produces a continuous electrical output having a magnitude proportional to the instantaneous amount of reflected light sensed by the photocell. The electrical output from the photocell can be used to drive a recorder which records measured reflectance, or the photocell output can be converted into a measurement of light absorption. In either of these instances the recorder is preferably calibrated to display percent reflectance or absorption based on the corresponding reflectance or absorption of a reference sample of oil shale of known kerogen concentration. Alternatively, the recorder can be calibrated to provide a direct reading of kerogen content, in gallons per ton, for example.

In the presently preferred system, the electrical output from the photocell 44 is connected by a line 54 to a chart recorder 56 which produces a continuous reading of light reflectance relative to the length of the core sample. The core sample drive motor 24 generates an output over a line 58 connected to the chart recorder 56 to synchronize movement of the paper drive (not shown) for the recorder chart 60 with the length of the core traveling through the housing 12. The recorder produces a trace 62 on the chart 60 in which reflectance from the photocell 44 is displayed on the Y axis of the chart relative to the length of the core, which is displayed along the X axis of the chart.

After being illuminated by the light source 38, the core sample 10 continuously passes through a second light-tight curtain 64 covering an exit opening 66 of the housing 12. The light-tight curtains 34 and 64 allow use of oversized entrance and exit openings 36 and 66, respectively, to accommodate core samples of different diameters.

Figure 4:
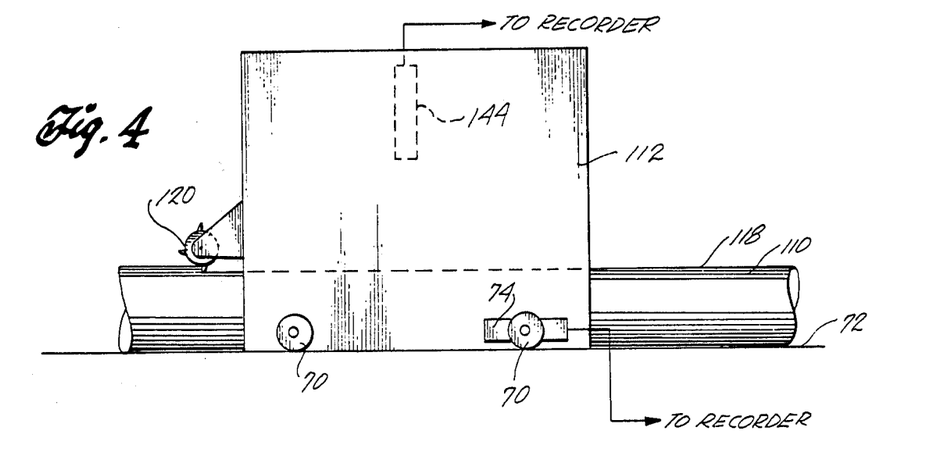
FIG. 4 is a fragmentary, schematic elevation view illustrating an alternate method of scanning the length of a core sample to measure kerogen content.

FIG. 4 schematically illustrates an alternate system for measuring kerogen content of a core sample 110 of oil shale. The alternate system includes a movable light-tight housing 112 using the same optical and electronic components described for the system illustrated in FIGS. 1 through 3. The movable system measures reflected light while traveling along the length of a core sample 110 maintained in a stationary position. The movable housing 112 is mounted on wheels 70 which roll on a flat substrate surface 72, such as a wood panel. A milling head 120 travels with the movable housing 112 to mill a narrow, flat reflective surface 118 along the top edge of the core sample 110 prior to the housing passing over the milled surface. A transducer 74 senses rotation of one of the rollers 70 of the housing 112 and generates an electrical output proportional to the longitudinal distance traveled by the housing. The output from the transducer 74 is connected to a chart recorder (not shown) along with an output signal from a photocell 144 in the housing 112. The chart recorder provides a measurement of light reflectance, or its equivalent, relative to the length of the core sample being analyzed. Means can be provided in the system of FIG. 4 to vary the elevation of the substrate surface 72 relative to the photocell 144, and other optical equipment within the housing 112, to accommodate core samples of different sizes.

Thus, in each of the systems described above, the position of the core sample can be adjusted relative to the optical system so that the reflective surfaces 18 and 118 will always be in a proper position to receive illumination over a selected area and so that the photocells receive only the light reflected from the selected area of illumination.

In using the field instrument illustrated in FIGS. 1 through 3, reflectance from a "reference" oil shale core sample is first measured to give a base line for the recorder or other monitoring system used. The reference core sample preferably comprises a barren piece of oil shale having a composition and grain size closely resembling the oil shale to be analyzed, but containing no kerogen. A magnesium oxide standard for 100% reflectance also can be used. A flat reflective surface is initially milled along the top edge of the reference core sample. The core sample is then passed through the housing 12 and into the path of filtered light from the light source 38. As described above, the light passing through the filter 40 is monochromatic, with the wavelength selected within the absorption band for kerogen in oil shale (preferably 420 nanometers). The light reflected from the reference core sample is measured by the photocell 44, and the reflectance from the reference sample establishes a scale reading of 100% (zero light absorption) for future measurements.

A large number of core samples of oil shale having a known kerogen content, say from previous chemical tests or the like, are analyzed using the same procedures and same monochromatic light wavelength as for the reference core sample. The reflectance of each core sample having a known composition is measured by the photocell 44, and these measurements are plotted, preferably in a graph showing the relationship between percent reflectance of each sample versus the known kerogen content of the sample. The graph can be used to determine the kerogen content of any core sample having an unknown kerogen content by simply measuring the reflectance from the surface of the core sample.

Figure 7:
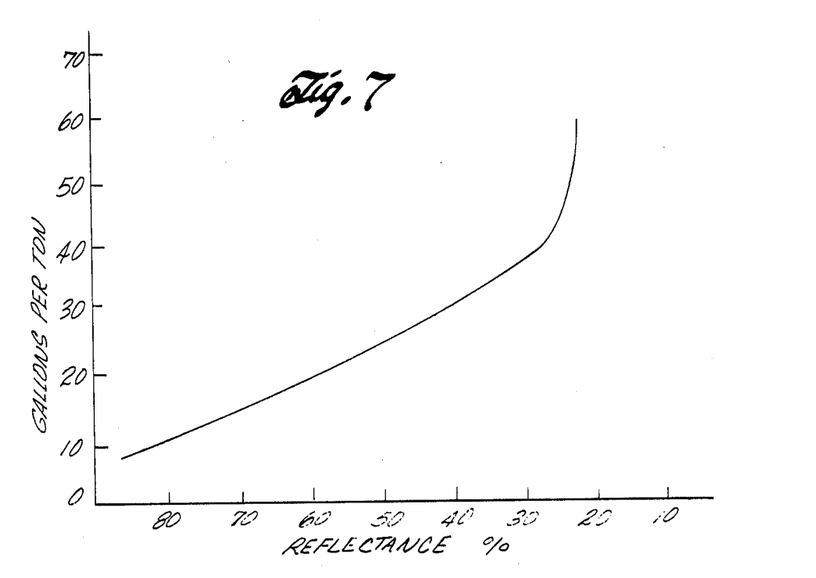
FIG. 7 is a graph illustrating the relationship between light reflectance and kerogen content of a core sample of oil shale.

FIG. 7 shows a graph obtained from measuring the reflectance of a number of oil shale core samples of known kerogen content. The samples were analyzed using Fischer assay techniques to determine their actual kerogen content. The reflectance measurements plotted were determined using oil shale reflectance at 420 nanometers wavelength with barren marlstone as the standard. The graph is a composite of data points derived from analyzing 24 core samples of varying kerogen content; and although some relatively high variations on opposite sides of the curve were present, the graph illustrates that there is a definite relationship between decreasing reflectance and increasing kerogen content up to about 40 to 45 gallons per ton at about 27% reflectance. Sensitivity of the tests were considered good in that 17 of the 24 tests yielded data points within 2 gallons per ton or 3 nanometers from the composite curve shown in FIG. 7. The graph illustrated in FIG. 7 can be used to determine the kerogen content of any core sample of unknown kerogen content if the core sample is analyzed with the same procedures and wavelength used to develop the graph in FIG. 7.

In the preferred monitoring system for the instruments illustrated in FIGS. 1 through 4, the recorder 56 plots percent reflectance as a function of the length of the core sample. The graph shown in FIG. 7 is then used to convert the percent reflectance measurements into measurements of kerogen content.

Figure 8:
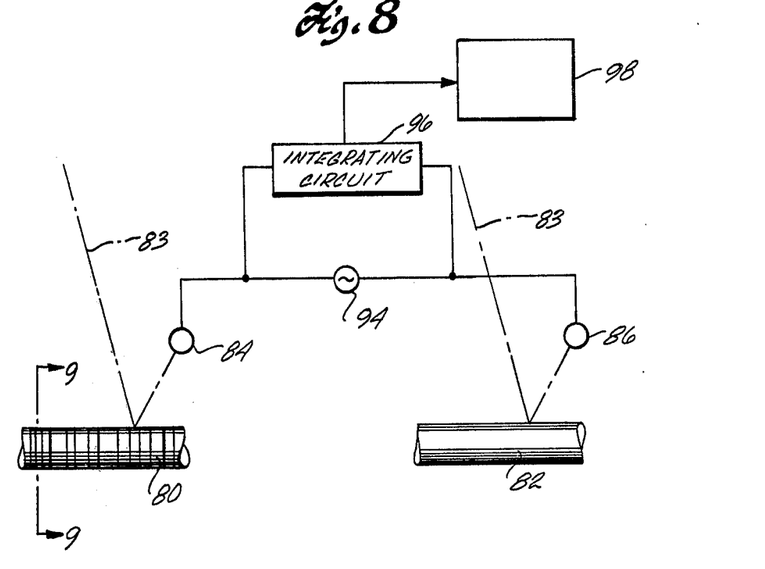
FIG. 8 is a schematic elevation view illustrating an alternate method for measuring the kerogen content of an oil shale core sample.
Figure 9:
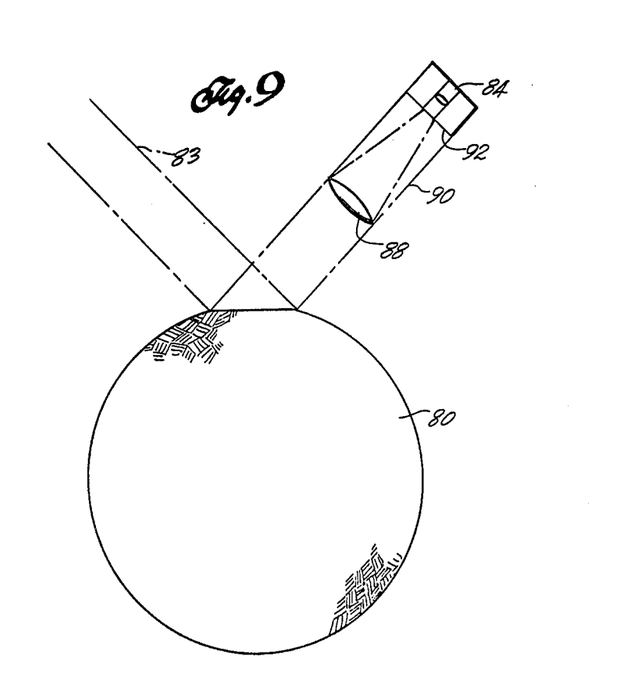
FIG. 9 is a schematic elevation view, partly in cross-section, taken on line 9—9 of FIG. 8.

FIGS. 8 and 9 illustrate an alternate form of the invention in which a core sample 80 of unknown kerogen content is continuously compared with a reference core sample 82 having a known kerogen content. Preferably, the reference core sample 82 is a barren piece of oil shale having zero kerogen content which produces a reference measurement of 100% reflectance along the length of the sample. The light source for illuminating each sample, as indicated by lines 83, can be white light from ambient sunlight, or an unfiltered light source, or a source of monochromatic light within the absorption band for kerogen in oil shale.

The reflectance from the unknown core sample 80 is sensed by a photocell 84, and the reflectance from the reference core sample 82 is sensed by a separate photocell 86. As represented for the unknown core 80 in FIG. 9, light reflected from each core sample passes through a corresponding lens 88 mounted at the front of a separate light-tight housing 90. The lenses focus reflected light on the corresponding photocells. A narrow bandpass filter 92 filters the light reflected from each sample to expose the photocells to monochromatic light having a wavelength sensitive to changes in kerogen content. As described above, the preferred light has a wavelength of 420 nanometers.

The photocell 84, together with its related focusing and filtering system, scans the length of the unknown core sample 80. Preferably, the photocell 86 and its related focusing and filtering system remains stationary to produce a constant zero standard reflectance reading. The two light sensing systems produce corresponding measurements of the instantaneous illumination sensed by the photocells. The output from each photocell is continuously fed to a null instrument 94, such as a galvanometer, which compares the instantaneous amount of light reflected from each core sample. Hence, increases in kerogen content of the unknown sample 80 are detected as increased deviations between the reflectance measurements from the two core samples.

The system illustrated in FIG. 8 includes means for integrating reflectance with respect to time, as opposed to the spatial integration system illustrated in FIGS. 1 through 4. In the system of FIG. 8, the output from the null instrument 94 is fed to an electrical integration circuit 96 which, in turn, produces an electrical output fed to a recorder 98. The integration circuit 96 can be any of a variety of electrical circuits capable of integrating, over a selected time interval, the reflectance measurements produced by the photocells 84 and 86. The integrating circuit 96 may include a time delay for sampling reflectance measurements during a time interval related to the amount of time required for the reflectance measuring system to travel a selected distance along each core sample. The magnitude of the output from the integration circuit 94 is proportional to the average amount of reflectance sensed during the selected time interval. This avoids wide variations in reflectance measurements produced by non-homogeneous kerogen distribution, as discussed above. The recorder 98 produces a continuous plot of integrated reflectance relative to the length of the core sample 80.

Thus, the invention makes it possible to obtain a quantitative, non-destructive analysis of the amount of a chemical component contained in a core sample, such as the kerogen content of oil shale. The analysis requires no calculations once the instruments are calibrated. The instruments can be used on core samples obtained directly from core drilling techniques, and allows workmen in the field to immediately analyze chemical content, rather than subjecting the core sample to laboratory tests which cause delays and may be destructive to the core sample. Thus, decisions on the progress of the core drilling program can be made in the field immediately after the core is recovered from the underground formation.

I claim:

1. A method for measuring the amount of a chemical component contained in a core sample comprising:
   illuminating a surface of a solid piece of the core sample with light;
   reflecting from the illuminated surface of the core sample a portion of said light not absorbed by the sample;
   providing relative movement between the core sample and a means for detecting reflected light to detect light reflected from an area of said illuminated surface;
   focusing light reflected from the illuminated surface area for integrating the reflected light over a sufficiently large area of the core sample surface to avoid amplitude variations in detected light due to non-uniform distribution of a chemical component contained in the core sample;
   detecting a monochromatic portion of the focused reflected light having a wavelength within the absorption band of said chemical component contained in the core sample; and
   indicating the integrated reflected light as a value proportional to the amount of said chemical component contained in the core sample.

2. The method according to claim 1 including forming on the core sample a reflective surface having a predetermined configuration; and thereafter illuminating said reflective surface.

3. The method according to claim 2 including forming a generally flat reflective surface of substantially uniform width along the length of the core sample; and thereafter detecting light reflected from only said flat reflective surface.

4. The method according to claim 2 including forming said reflective surface along the length of an elongated core sample; and varying the location of said area of illumination lengthwise with respect to said elongated core sample.

5. The method according to claim 1 including generating a first output representative of the amount of light reflected from a surface of a first core sample having a chemical component of known concentration; generating a second output representative of the amount of light reflected from a surface of a second core sample having a chemical component of unknown concentration; and comparing the first and second outputs to produce an indication representative of the amount of said chemical component contained in the second core sample.

6. The method according to claim 5 including integrating the amount of light reflected from a selected area of the second core sample to produce said second output; determining the amount of light reflected from a corresponding area of the first core sample to produce said first output; and comparing the first and second outputs to provide an indication of the amount of said chemical component with respect to said selected area of the second core sample.

7. The method according to claim 1 including moving the light detecting means relative to the core sample.

8. The method according to claim 1 including moving the core sample relative to the light detecting means.

9. The method according to claim 1 including filtering the reflected light to pass monochromatic light within a narrow wavelength band, and detecting the filtered monochromatic light.

10. The method according to claim 9 including selecting the wavelength of the filtered monochromatic light to correspond to the selected chemical component in the core sample.

11. The method according to claim 1 including varying the location of said illuminated surface lengthwise with respect to an elongated core sample, and detecting the light reflected from each location.

12. The method according to claim 11 including indicating the detected light as a value proportional to the content of said chemical component with respect to the length of the core sample.

13. The method according to claim 11 including intermittently varying the location of said illuminated surface and detecting the light reflected from each location.

14. A method for measuring the amount of a chemical component contained in a core sample comprising:
   forming on a solid piece of the core sample a reflective surface of a generally uniform configuration;
   illuminating said reflective surface with light;
   reflecting from the illuminated surface a portion of said light not absorbed by the sample;
   integrating the light reflected from the core sample by focusing light reflected from a sufficiently large area of the core sample surface to avoid amplitude variations in detected light due to non-uniform distribution of a chemical component contained in the core sample;
   detecting a monochromatic portion of said focused reflected light having a wavelength within the absorption band of said chemical component contained in the core sample; and
   indicating the amount of focused detected light as a value proportional to the amount of said chemical component contained in the core sample.

15. The method according to claim 14 including forming a generally flat reflective surface of substantially uniform width along the length of the core sample; and thereafter detecting light reflected from only said flat reflective surface.

16. Apparatus for measuring the amount of a chemical component contained in a core sample comprising:

means for illuminating a surface of a solid piece of a core sample with light;

means for detecting monochromatic light having a wavelength within the absorption band of a selected chemical component contained in the core sample;

means for providing relative movement between an elongated piece of said core sample and the light detecting means for reflecting a portion of light not absorbed by the core sample from said means for illuminating the surface to the light detecting means so as to detect reflected light relative to the length of the core sample;

means for integrating the reflected light over a sufficiently large area of the core sample to avoid amplitude variations in detected light due to non-uniform distribution of said chemical component contained in the core sample, the light integrating means including means for focusing on the light detecting means the light reflected from said illuminated surface area for sensing the amount of said focused reflected light, and means responsive to the light detecting means to produce a measurement of the average amount of light reflected from said illuminated surface area; and means for indicating the amount of integrated detected light as a value proportional to the amount of said chemical component contained in the core sample.

17. Apparatus according to claim 16 including means for forming on the core sample a reflective surface of a generally uniform predetermined configuration; and means for thereafter illuminating said reflective surface.

18. Apparatus according to claim 17 including means for forming a generally flat reflective surface of substantially uniform width along the length of the core sample; and thereafter detecting light reflected from only said flat reflective surface.

19. Apparatus according to claim 16 in which the indicating means comprises first sensing means for detecting relative movement between the core sample and the light detecting means, second sensing means for detecting the amount of said reflected light, and means responsive to the first and second sensing means for producing an indication of the amount of reflected light with respect to the length of the core sample.

20. Apparatus according to claim 16 including a light-tight housing for receiving an elongated core sample to be analyzed; means for mounting the light source in the housing to direct light onto said surface of the core sample; and means mounting the light detecting means within the housing to sense the light reflected from the core sample.

21. Apparatus according to claim 20 including a light filter disposed in the housing between the light detecting means and the illuminated surface of the core sample to pass said monochromatic portion of the reflected light.

22. Apparatus according to claim 21 including means for removing the filter from said housing to adjust the wavelength of said monochromatic light.

23. Apparatus according to claim 20 including an elongated light source for illuminating an elongated surface area of the core sample.

24. Apparatus according to claim 23 including means disposed within the housing for focusing on the light detecting means the light reflected from said illuminated area.

25. Apparatus according to claim 23 including means for varying the location of the surface area of the core sample exposed to the light source.

26. Apparatus according to claim 20 including means carried on an exterior portion of the housing for forming reflective surface of predetermined configuration along the length of an elongated core sample prior to the core sample being illuminated by the light source.

27. Apparatus according to claim 20 including means for feeding a core sample through the housing.

28. Apparatus according to claim 20 including means for moving the housing lengthwise relative to an elongated core sample.

29. Apparatus according to claim 16 in which the indicating means comprises means for comparing the amount of light reflected from said core sample with a corresponding amount of light reflected from a core sample having a known content of said selected chemical component.

30. Apparatus according to claim 29 including means responsive to the comparing means for indicating the compared amounts of reflected light.

31. Apparatus for measuring the amount of a chemical component contained in a core sample, comprising:

means for forming on a solid piece of a core sample a reflective surface of generally uniform configuration;

means for illuminating said reflective surface with light;

means for detecting monochromatic light having a wavelength within the absorption band of a selected chemical component contained in the core sample;

means for reflecting a portion of light not absorbed by the core sample from said means for illuminating the surface to the light detecting means;

means for integrating the reflected light over a sufficiently large area of the core sample to avoid amplitude variations in detected light due to non-uniform distribution of said chemical component contained in the core sample, the light integrating means including means for focusing on the light detecting means the light reflected from said illuminated surface area for sensing the amount of said focused reflected light to provide a measurement of the average amount of light reflected from said illuminated surface area; and means for indicating the amount of integrated detected light as a value proportional to the amount of said chemical component contained in the core sample.

32. Apparatus according to claim 31 including means for forming a generally flat reflective surface of substantially uniform width along the length of the core sample; and thereafter detecting light reflected from only said flat reflective surface.

33. Apparatus according to claim 31 including means for providing relative movement between an elongated piece of said core sample and the light detecting means so as to detect reflected light relative to the length of the core sample.

34. Apparatus according to claim 33 in which the indicating means comprises first sensing means for detecting relative movement between the core sample and the light detecting means, second sensing means for detecting the amount of reflected light, and means responsive to the first and second sensing means for producing an indication of the amount of reflected light with respect to the length of the core sample.

35. Apparatus according to claim 31 including a light-tight housing for receiving an elongated core sample to be analyzed; means for mounting the light source in the housing to direct light onto said surface of the core sample and to reflect the light not absorbed by the sample; means for mounting the light detecting means within the housing to sense the light reflected from the core sample; and means disposed outside the housing for forming said reflective surface along the length of an elongated core sample prior to the core sample being illuminated by the light source.

36. Apparatus according to claim 35 including a light filter disposed in the housing between the light detecting means and the illuminated surface of the core sample to pass said monochromatic portion of the reflected light.

37. Apparatus according to claim 36 including means for removing the filter from said housing to provide means for adjusting the wavelength of said monochromatic light.

38. Apparatus according to claim 35 including an elongated light source for illuminating an elongated surface area of the core sample.

39. Apparatus according to claim 38 including means disposed within the housing for focusing on the light detecting means the light reflected from said illuminated area.

40. Apparatus according to claim 39 including a light filter disposed in the housing between the light detecting means and the illuminated surface of the core sample to pass said monochromatic portion of the reflected light.

41. Apparatus according to claim 40 including means for changing the filter in said housing to adjust the wavelength of said monochromatic light.

42. Apparatus according to claim 41 including means for forming on said core sample a generally flat reflective surface of substantially uniform width prior to illuminating said reflective surface.

43. Apparatus for measuring the amount of a chemical component contained in a core sample comprising:
 a light-tight housing for receiving an elongated core sample to be analyzed;
 means mounting a light source in the housing to direct light onto a sufficiently large surface area of the core sample to avoid amplitude variations in detected light due to non-uniform distribution of a chemical component contained in the core sample;
 means mounting a light detecting means in the housing to detect monochromatic light having a wavelength within the absorption band of said chemical component contained in the core sample;
 means for reflecting a portion of light not absorbed by said selected surface area of the core sample from the light source to the light detecting means;
 means for focusing on the light detecting means the light reflected from said selected surface area for sensing the amount of focused reflected light; and
 means for indicating the amount of detected light as a value proportional to the average concentration of said chemical component in said selected surface area of the core sample.

44. Apparatus according to claim 43 including an elongated light source for illuminating an elongated surface area of the core sample.

45. Apparatus according to claim 44 including means disposed within the housing for focusing on the light detecting means the light reflected from said illuminated area.

* * * * *